United States Patent
Kostrzewski et al.

(10) Patent No.: US 9,833,292 B2
(45) Date of Patent: *Dec. 5, 2017

(54) ROBOTIC SYSTEM AND METHOD FOR SPINAL AND OTHER SURGERIES

(71) Applicant: KB MEDICAL SA, Audubon, PA (US)

(72) Inventors: Szymon Kostrzewski, Lausanne (CH); Philippe Berard, Chavannes-pres-Renens (CH); Charles Baur, Saint-Aubin-Sauges (CH); John Michael Duff, La Croix-sur-Lutry (CH); Kishore Sandu, Savigny (CH)

(73) Assignee: Globus Medical, Inc., Audubon, PA (US)

( * ) Notice: Subject to any disclaimer, the term of this patent is extended or adjusted under 35 U.S.C. 154(b) by 23 days.

This patent is subject to a terminal disclaimer.

(21) Appl. No.: 14/824,602

(22) Filed: Aug. 12, 2015

(65) Prior Publication Data

US 2016/0038238 A1    Feb. 11, 2016

Related U.S. Application Data

(63) Continuation of application No. 14/522,509, filed on Oct. 23, 2014, now Pat. No. 9,125,680, which is a
(Continued)

(51) Int. Cl.
*A61B 17/56* (2006.01)
*A61B 17/70* (2006.01)
(Continued)

(52) U.S. Cl.
CPC ............ *A61B 34/20* (2016.02); *A61B 5/1127* (2013.01); *A61B 17/1671* (2013.01);
(Continued)

(58) Field of Classification Search
CPC ............ A61B 19/2203; A61B 19/5244; A61B 2019/507; A61B 2017/00694
See application file for complete search history.

(56) References Cited

U.S. PATENT DOCUMENTS

| 4,166,602 A | 9/1979 | Nilsen et al. |
| 4,799,779 A | 1/1989 | Mesmer |

(Continued)

FOREIGN PATENT DOCUMENTS

| DE | 10003051 A1 | 8/2001 |
| EP | 1693011 A1 | 8/2006 |

(Continued)

OTHER PUBLICATIONS

Rosa Is a New Stereotactic Neurological Surgery Robot. Neurological Surgery. Jun. 13, 2011 (http://www.medgadget.com/2011/06/rosa-neuro-surgery-robot.html).
(Continued)

*Primary Examiner* — Zade Coley

(57) ABSTRACT

The present invention relates to a method, such as a surgical method for assisting a surgeon for placing screws in the spine using a robot attached to a passive structure. The present invention also related to a method, such as a surgical method for assisting a surgeon for removing volumes in the body of a patient using a robot attached to a passive structure and to a device to carry out said methods.
The present invention further concerns a device suitable to carry out the methods according to the present invention.

17 Claims, 8 Drawing Sheets

Related U.S. Application Data continuation of application No. 14/009,050, filed as application No. PCT/IB2012/051611 on Apr. 2, 2012, now Pat. No. 9,308,050.

(60) Provisional application No. 61/470,545, filed on Apr. 1, 2011.

(51) Int. Cl.

| | |
|---|---|
| *A61B 34/20* | (2016.01) |
| *A61B 34/00* | (2016.01) |
| *A61B 5/11* | (2006.01) |
| *A61B 17/16* | (2006.01) |
| *A61B 17/17* | (2006.01) |
| *A61B 17/86* | (2006.01) |
| *A61B 19/00* | (2006.01) |
| *A61B 90/57* | (2016.01) |
| *A61B 34/30* | (2016.01) |
| *A61B 34/10* | (2016.01) |
| *A61B 17/00* | (2006.01) |

(52) U.S. Cl.
CPC ...... *A61B 17/1703* (2013.01); *A61B 17/7082* (2013.01); *A61B 17/86* (2013.01); *A61B 19/26* (2013.01); *A61B 34/30* (2016.02); *A61B 34/76* (2016.02); *A61B 90/57* (2016.02); *A61B 2017/00694* (2013.01); *A61B 2019/464* (2013.01); *A61B 2019/5257* (2013.01); *A61B 2019/5437* (2013.01); *A61B 2019/5483* (2013.01); *A61B 2034/107* (2016.02); *Y10S 901/03* (2013.01); *Y10S 901/09* (2013.01)

(56) References Cited

U.S. PATENT DOCUMENTS

| | | | |
|---|---|---|---|
| 5,408,409 A * | 4/1995 | Glassman | B25J 9/1679 128/920 |
| 5,948,002 A | 9/1999 | Bonutti | |
| D435,107 S | 12/2000 | Blair et al. | |
| D456,080 S | 4/2002 | Karlsson | |
| D461,484 S | 8/2002 | Kraft | |
| 6,451,027 B1 | 9/2002 | Cooper et al. | |
| 6,604,021 B2 | 8/2003 | Imai et al. | |
| D506,257 S | 6/2005 | Smith | |
| D528,216 S | 9/2006 | Korner | |
| 7,155,316 B2 * | 12/2006 | Sutherland | A61B 19/22 318/568.11 |
| 7,196,454 B2 * | 3/2007 | Baur | H02N 2/025 310/323.01 |
| D548,759 S | 8/2007 | Kraft | |
| D553,655 S | 10/2007 | Jennings et al. | |
| D572,739 S | 7/2008 | Jennings et al. | |
| D646,703 S | 10/2011 | Wong | |
| D654,503 S | 2/2012 | Sapper | |
| D655,324 S | 3/2012 | Wong | |
| D660,845 S | 5/2012 | Schmauch et al. | |
| D679,016 S | 3/2013 | Jarva | |
| D685,479 S | 7/2013 | Charles | |
| 8,509,503 B2 | 8/2013 | Nahum et al. | |
| D690,421 S | 9/2013 | Charles | |
| D692,139 S | 10/2013 | Charles | |
| D702,841 S | 4/2014 | Wyrozub | |
| D708,332 S | 7/2014 | Kim | |
| D724,738 S | 3/2015 | Dorris et al. | |
| 9,125,680 B2 | 9/2015 | Kostrzewski et al. | |
| 9,308,050 B2 | 4/2016 | Kostrzewski et al. | |
| 2003/0097060 A1 | 5/2003 | Yanof et al. | |
| 2004/0034282 A1 | 2/2004 | Quaid | |
| 2004/0128026 A1 | 7/2004 | Harris et al. | |
| 2004/0143168 A1 | 7/2004 | Hu et al. | |
| 2005/0245817 A1 | 11/2005 | Clayton et al. | |
| 2006/0036264 A1 | 2/2006 | Selover et al. | |
| 2006/0142657 A1 * | 6/2006 | Quaid | A61N 1/372 600/424 |
| 2006/0161136 A1 * | 7/2006 | Anderson | A61B 90/57 606/1 |
| 2006/0161138 A1 | 7/2006 | Orban et al. | |
| 2007/0005189 A1 | 1/2007 | Furubo | |
| 2007/0032906 A1 * | 2/2007 | Sutherland | A61B 19/22 700/248 |
| 2007/0055291 A1 | 3/2007 | Birkmeyer et al. | |
| 2007/0119123 A1 | 5/2007 | Clark et al. | |
| 2007/0156157 A1 * | 7/2007 | Nahum | A61B 17/154 606/130 |
| 2007/0270685 A1 * | 11/2007 | Kang | A61B 19/5244 600/424 |
| 2008/0215181 A1 | 9/2008 | Smith et al. | |
| 2008/0221520 A1 | 9/2008 | Nagel et al. | |
| 2008/0287862 A1 | 11/2008 | Weitzner et al. | |
| 2009/0088848 A1 | 4/2009 | Martz et al. | |
| 2009/0326318 A1 * | 12/2009 | Tognaccini | A61B 1/00183 600/104 |
| 2010/0166496 A1 | 7/2010 | Bennett et al. | |
| 2010/0192720 A1 * | 8/2010 | Helmer | B25J 17/0266 74/490.06 |
| 2010/0210939 A1 | 8/2010 | Hartmann et al. | |
| 2010/0319713 A1 | 12/2010 | Byers et al. | |
| 2011/0082462 A1 | 4/2011 | Suarez et al. | |
| 2011/0087238 A1 | 4/2011 | Wang et al. | |
| 2011/0126844 A1 | 6/2011 | Cinquin et al. | |
| 2011/0190789 A1 * | 8/2011 | Thiran | A61B 17/1739 606/130 |
| 2012/0059378 A1 * | 3/2012 | Farrell | A61B 17/1626 606/80 |
| 2013/0081636 A1 | 4/2013 | Schuele | |
| 2013/0113798 A1 | 5/2013 | Nahum et al. | |
| 2013/0172902 A1 | 7/2013 | Lightcap et al. | |
| 2013/0317344 A1 | 11/2013 | Borus et al. | |
| 2014/0052151 A1 | 2/2014 | Hingwe et al. | |
| 2014/0066944 A1 | 3/2014 | Taylor et al. | |
| 2014/0121676 A1 | 5/2014 | Kostrzewski et al. | |
| 2015/0032164 A1 | 1/2015 | Crawford et al. | |
| 2015/0045764 A1 | 2/2015 | Kaplan et al. | |
| 2015/0045813 A1 | 2/2015 | Kostrzewski et al. | |
| 2015/0100066 A1 | 4/2015 | Kostrzewski et al. | |
| 2015/0196365 A1 | 7/2015 | Kostrzewski et al. | |
| 2015/0202009 A1 | 7/2015 | Nussbaumer et al. | |
| 2015/0223897 A1 | 8/2015 | Kostrzewski et al. | |
| 2015/0305817 A1 | 10/2015 | Kostrzewski | |

FOREIGN PATENT DOCUMENTS

| | | | |
|---|---|---|---|
| WO | WO-98/02107 A1 | 1/1998 | |
| WO | WO-2004/014244 A2 | 2/2004 | |
| WO | WO-2005/122916 A1 | 12/2005 | |
| WO | WO 2005122916 A1 * | 12/2005 | .......... A61B 17/154 |
| WO | WO-2006/091494 A1 | 8/2006 | |
| WO | WO-2007/136768 A2 | 11/2007 | |
| WO | WO 2007136768 A2 * | 11/2007 | .......... A61B 34/71 |
| WO | WO-2008/097540 A2 | 8/2008 | |
| WO | WO 2008097540 A2 * | 8/2008 | .......... A61B 7/0503 |
| WO | WO-2009/013406 A2 | 1/2009 | |
| WO | WO-2012/131660 A1 | 10/2012 | |
| WO | WO-2012/133912 A1 | 10/2012 | |
| WO | WO-2013/079843 A1 | 6/2013 | |
| WO | WO-2013/098496 A1 | 7/2013 | |
| WO | WO-2013/160239 A1 | 10/2013 | |
| WO | WO-2013/192598 A1 | 12/2013 | |
| WO | WO-2015/049109 A1 | 4/2015 | |
| WO | WO-2015/107099 A1 | 7/2015 | |
| WO | WO-2015/110542 A1 | 7/2015 | |
| WO | WO-2015/121311 A1 | 8/2015 | |
| WO | WO-2015/162256 A1 | 10/2015 | |

OTHER PUBLICATIONS

Zemiti, N. et al., A new Robot for Force Control in Minimally Invasive Surgery. Proceedings of 2004 IEEE/RSJ International

(56) References Cited

OTHER PUBLICATIONS

Conference on Intelligent Robots and Systems, 4:3643-3648 (2004).
International Search Report for PCT/IB2012/051607, 6 pages (dated Aug. 8, 2012).
International Search Report for PCT/IB2012/051611, 6 pages (dated Aug. 14, 2012).

* cited by examiner

```
the user can proceed with the desired surgical procedure
                            ↑
┌─────────────────────────────────────────────────────────┐
│ when the screw trajectory is inside the robot's         │
│ workspace the robot starts to automatically follow it   │
│ in real-time i.e. the vertebrae and the robot positions │
│ are measured and if one of them moves the robot may     │
│ change the position of the tool to compensate           │
└─────────────────────────────────────────────────────────┘
                            ↑
┌─────────────────────────────────────────────────────────┐
│ the user blocks the structure holing robot such that it │
│ will be rigidly held in place                           │
└─────────────────────────────────────────────────────────┘
                            ↑
┌─────────────────────────────────────────────────────────┐
│ the user unblocks the structure of the robot and        │
│ manually moves the robot to a position indicated by the │
│ navigation software;                                    │
└─────────────────────────────────────────────────────────┘
                            ↑
┌─────────────────────────────────────────────────────────┐
│ an ideal, or at least a suitable robot position is      │
│ shown with an indicator (e.g. change of color) by the   │
│ navigation software                                     │
└─────────────────────────────────────────────────────────┘
                            ↑
┌─────────────────────────────────────────────────────────┐
│ after an optical marker of an optical tracking          │
│ system is attached to a vertebrae the patient's         │
│ position is registered                                  │
└─────────────────────────────────────────────────────────┘
                            ↑
```

FIG. 5

ROBOTIC SYSTEM AND METHOD FOR SPINAL AND OTHER SURGERIES

CORRESPONDING APPLICATION

The present application claims the priority of U.S. application 61/470,545 filed on Apr. 1, 2011, the content of which is incorporated by reference in its entirety in the present application.

FIELD OF THE INVENTION

The present invention concerns a robotic system and methods for surgical procedures. More specifically, the present invention concerns methods for assisting the surgeon to carry out a surgical procedure using a robotic system and computer means.

BACKGROUND OF THE INVENTION

Spine Surgeries

Background

Spine surgeries often use fixations and implants attached to vertebrae using screws. It is important to place the screws properly so they do not touch or violate neither spinal cord nor arteries. It can be a difficult task due to the needed precision, high density and constrained access to the vertebrae. For these reasons surgeons use support systems that can enhance the accuracy of the screw placement.

In spine surgeries there are the following methods used for placing the screws:
1. Purely manual
2. Manual using navigation systems
3. Using robotic systems Manual Methods In the traditional manual technique, a surgeon on the basis of the pre-operative CT scans visually judges the screw trajectory. During drilling, the fluoroscopic images are taken to verify if the trajectory is correct. An advantage of this technique is that except standard reconstruction systems no additional tools are needed and it can be always used in case of an emergency. On the other hand it strongly relies on the surgeon's experience and can be subject to his changing predisposition. Security is also doubtful as the fluoroscopic images are taken only after the drilling is done. The accuracy and information shown on those images can also vary. Drilling is technically difficult because the tools are held in hand. Surgeon needs to have a very good coordination and be able to simultaneously do many tasks. Due to those disadvantages a screw misplacement rate on the level of 30-50% in the cervical spine was reported.

Manual Methods Using Navigation Systems

Navigation systems can measure the position of surgical tools and a patient in the operating room. Currently most often the optical tracking is used for measurements but other methods such as electro-magnetic tracking can be used. Procedures involving those systems will be referred as the image-guided surgeries. Because of the improved accuracy image-guided procedures made the screw placement in the cervical spine possible for certain patients. The image-guided surgeries in the spinal domain are still done manually. For this reason the surgical tools though tracked can be wrongly positioned because of the human constraints. Precision can be a subject of a variable human factor. These techniques demand increased attention from the surgeon as he needs to coordinate operations with virtual indications on the screen. In case of a procedural error big inaccuracies can appear and for this reason a staff training is important. Problems with the verification of the registration accuracy are common.

Methods Using Robotic Systems

Few attempts have been done to introduce robotic systems for spinal surgeries. One of them is developed at the German Aerospace Center (DLR) Miro/KineMedic robotic system. It is designed for a surgical telemanipulation. The robotic part of the system consists of three lightweight robotic arms. Each joint is equipped with a force sensor and uses a sophisticated control system with the force feedback and the gravity compensation. The robot's redundancy is used for the workspace optimization and allows to fulfill additional criterias in the operating room. Proposition of the possible setup for a pedicle screw placement with the Miro/KineMedic system would consist of the DLR lightweight robotic arm, an optical tracking system and the software. The surgeon plans the surgery in advance. In the operating room several robot control modes are available. Initially the robotic arm is moved to the planned position by the surgeon using a hands-on impedance control. When it is in place, the surgeon can start drilling using a driller held by a passive tool holder attached to the robot's end effector. The robot compensates for the position errors while surgeon does axial movement. Authors do not specify in which parts of a spine the robot could work. The proposed registration method using a surface matching only could be insufficient in a general situation as those algorithms need a good starting point and converge to the closest local minimum. It is not specified if in this system standard surgical reconstruction tools could be used which can be crucial for the acceptance in the medical domain. A relatively big robotic arm can have disadvantages in a dense environment of an operating room. It is not said how it would be interfaced with the equipment of an operating room. Sophisticated impedance-control algorithms can be difficult to certify in the medical domain and till now no such arm was certified. Expected accuracy of the system is not mentioned. Accordingly to the author's knowledge no further publications concerning this proposition are available.

Other robotic system for the spinal surgery is the Mazor's SmartAssist. It consists of a miniature robot attached to the spine with a base platform and a workstation for planning and navigation. Registration is based on the matching between pre-operative CT scans and intra-operative fluoroscopic images acquired with a calibrated device. In the next step the robot moves to planned spacial position and the surgeon performs a surgery via the tool guide. The robot does not move during the intervention acting as a tool holder (passive guidance). The system was tested with good results. The SpineAssist can be used only in the thoracic and lumbar parts and can not be used in the cervical spine where high accuracy is most important. Fluoroscopic registration has certain disadvantages and needs a calibrated C-Arm. Possible hard to detect errors were reported. The robotic arm does not compensate for random vertebral movements while drilling. Drill slippage on the surface of the vertebrae causing big inaccuracies was reported.

Another robotic system for spinal surgery is the Cooperative Robotic Assistant. It consists of a 6 degree of freedom robot with a kinematically closed structure. It uses a new drill-by-wire mechanism for placing the screws and uses a 1 degree of freedom haptic device to provide the force feedback for the surgeon. Achieved accuracy below 1 [μm] of the robotic part was reported. Authors claim that closed construction was chosen for rigidity reasons. The robot is taking a lot of space in the operating room. Equipment of the operating room should be strongly adapted to be used with this system. The drill-by-wire mechanism needs its own tools which can be a limit for acceptance in the medical field. The system does not perform any external measurements so nothing about registration methods is known. The precision of the registration will strongly influence the accuracy of the robotic arm measured separately. Other robotic system is the Spinebot system for the lumbar spine surgery. It consists of a 3 degree of freedom positioner, gimbals and drilling tool having 2 degree of freedom each. It uses an optical tracking system for registration and measurements. Big advantage of the system is that during the surgery holes in spine can be drilled percutaneusly (through the skin). The system can work only in lumbar part of the spine. In this area needed accuracy is much lower than in cervical part and access is easier.

SUMMARY OF THE INVENTION

An aim of the present invention is to improve the known systems and methods.

The invention will be described in more detail in the following specification and with reference to the drawings which show:

FIG. 1 illustrates the different elements of a proposed robotic system for spinal surgeries;

FIGS. 2(*a*) and 2(*b*) illustrate an example of patient registration;

FIGS. 3(*a*) and 3(*b*) illustrate the indicators helping the surgeon to position the robot;

FIG. 5 illustrates a block diagram of the method in one embodiment;

Figure 1:
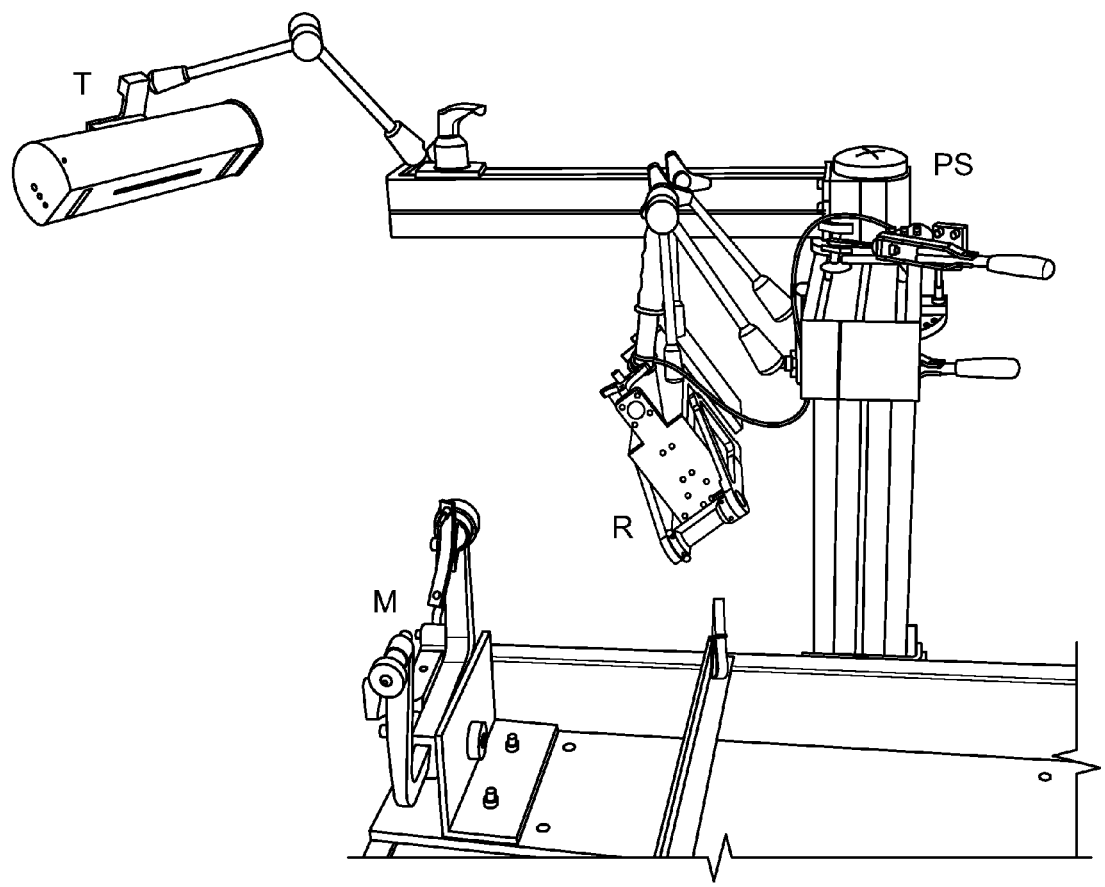

In an embodiment the invention concerns a method for assisting a user for placing screws in the spine of a patient using a robot attached to a passive structure and holding a tool, wherein said method comprises the following steps:

after a marker of an tracking system is attached to a vertebrae the patient's position is registered in that the transformation between the position of the vertebrae and of the attached marker and/or planning is found the robot is positioned such that the planned screw trajectory is inside the robot's workspace by moving the passive structure;

a navigation software assists the user in doing this task, whereby the user unblocks structure of the robot and manually moves the robot to a position indicated by the navigation software;

a target robot position, or at least a suitable robot position is determined;

in this case the user may block the passive structure such that it will be rigidly held in place;

when the screw trajectory is inside the robot's workspace the robot starts to automatically follow it in real-time i.e. the vertebrae and the robot positions are measured and if one of them moves the robot will change the position of the tool to compensate;

the user can proceed with the desired surgical procedure.

In an embodiment, the invention concerns a method for assisting a user for removing volumes in the body of a patient using a robot attached to a passive structure and holding a tool, wherein said method comprises the following steps:

after a marker of the tracking system is attached to the patient the patient' position is registered in that the transformation between the position of the volumes and of the attached marker is found;

the robot is positioned such that the planned volume(s) to be removed is (are) inside the robot's workspace by moving the passive structure;

a navigation software assists the user in doing this task, whereby the user unblocks the passive structure and manually moves the robot to the position indicated by the navigation software;

a target robot position, or at least suitable, robot position is determined;

in this case the user may block the passive structure such that the robot will be rigidly held in place;

when the volume(s) to be removed is (are) are in the robot's workspace the robot starts to automatically compensate for the patient movements in real-time i.e. marker and the robot positions are measured and if one of them moves the robot will change the position of the tool to compensate;

the user can proceed with the standard surgical procedure whereby the navigation software controls the robot's position so that the tool held by the robot (driller or shaver) does not violate the "no-go" zones defined during planning.

In an embodiment, the methods comprise a haptic interaction of the surgeon with the device.

In an embodiment the user feels repulsive/wall-like forces on the haptic device when the tool approaches the "no-go" zone.

In an embodiment the volumes to be removed (stay-in zones) and volumes that must be protected (no-go zones) are defined preoperatively or intra-operatively.

In an embodiment if the user wants to remove certain volumes he enters it with the tool and inside said volume the tool remains blocked inside until he explicitly wants to leave it ("stay-in" volume).

In an embodiment when the tool stays inside the stay-in volume the user feels repulsive/wall-like forces that prevent him from leaving the volume.

In an embodiment margins of interaction around the "no-go" and "stay-in" zones can be defined.

In an embodiment the coupling between the haptic device movements and the robot movements is definable to allow the user to have small movements/high precision or big movements/high speed.

In an embodiment automatic compensation of the patient's movement is switched off and is done manually by the user.

In an embodiment the target position of the robot or at least a suitable robot position is determined as a semi-transparent phantom image (indicator) on a screen, and the phantom is in a first color at the beginning and changes to another color when the robot's workspace contains the screw trajectory or when the robot's workspace contains the volume to be removed. Other indicators may be used.

In an embodiment the invention concerns a device comprising at least a surgery planning software, a robotic system, comprising an active robot and a passive structure for positioning the active robot and a controller, a measurement system for real-time patient and robot position measurements and position tracking, and a workstation with a navigation software controlling the device and for providing feedback to the user.

In an embodiment the workstation is a computer, such as a personal computer.

In an embodiment a computer contains the surgery planning software and monitors the measurement system.

In an embodiment the active robot covers a small volume and the passive structure covers a large volume.

DETAILED DESCRIPTION OF THE INVENTION

Spine Surgery

The robotic system described in this part is used to assist the surgeon while placing the screws into a vertebrae, as a practical example. The system comprises the following elements (see also FIG. 7):

1. A surgery planning software (known in principle in the art)

a) the planning is based on medical images obtained pre-operatively (CT, MRI or other methods)

b) the planning software allows the surgeon to define needed data for the surgery which can be: screw trajectories and data for the registration. The planning software can suggest the surgeon the best trajectories for the screws c) if the point to point followed by the surface matching registration method is used the surgeon defines landmarks (natural or artificial) and generates a 3D model of the vertebrae Alternatively, it is possible to use the following system without the explicit pre-operative planning. In such case, the user/surgeon inter-operatively decides about the trajectory based on his experience and/or medical images.

2. Compact robot with sufficient accuracy and rigidity. The corresponding robotic system is disclosed in parallel applications EP No 11160893.1 filed on Apr. 1, 2011 and PCT application No PCT/IB2012/051607, filed on Apr. 2, 2012, both in the name of the same Applicant as the present application and the content of which is incorporated by reference in its entirety in the present application.

a) the robot positions or helps to position surgical tools b) the robot has sufficient number of degrees of freedom to define the screw trajectories in space, c) the robot's absolute accuracy should be the same or better than the accuracy provided by the optical tracking, medical imaging and application requirements. For example, this accuracy could be around 0.1 mm.

d) the robot's rigidity should be sufficient to ensure the robot's accuracy while the surgeon operates the tools, the robot's workspace should be big enough so that manual positioning of the robot (using the passive structure) is simple, 3. Robot's controller (see the robotic system disclosed in applications EP No 11160893.1 filed on Apr. 1, 2011 and PCT application No PCT/IB2012/051607 filed on Apr. 2, 2012 mentioned above)

a) controls the robot's end effector position and/or velocity and/or force, b) can have different control modes: position, velocity, torque.

4. Passive structure positioning the robot in space (see the robotic system disclosed in applications EP No 11160893.1 filed on Apr. 1, 2011 PCT application No PCT/IB2012/051607 filed on Apr. 2, 2012 mentioned above), a) the passive structure can be in a blocked state holding the robot rigidly in space or in an unblocked state allowing the surgeon to freely position (manually by the surgeon) the robot in space, b) the passive structure extends the robot's workspace and should be designed so that all required tool positions can be achieved, c) the passive structure's rigidity should be sufficient so that the system composed of the passive structure and the robot has the required accuracy while the surgeon operates the tools, d) it should be possible to integrate the passive structure with the equipment in the operating room e) to simplify the usage of the passive structure it can have additional features like: a gravity compensation, a manipulation adapted to one person, a feasible blocking/unblocking interface (ex. pedals)

5. Measurement system for real-time patient and robot position measurements (see the robotic system disclosed in applications EP No 11160893.1 filed on Apr. 1, 2011 and PCT application No PCT/IB2012/051607 filed on Apr. 2, 2012 mentioned above)

a) different measurement systems can be used known in principle in the art: electromagnetic, fixed (when target bone/tissue position is fixed and robot arm is used to register it), template-based and others. The most popular is an optical tracking, with appropriate markers.

b) the optical tracking system comprises for example a camera, markers (attached to the robot and the patient) and a pointer (which can measure a single point in space), c) precision of the optical tracking system should be sufficient to fulfill the system requirements. For example it should be around 0.2 mm.

d) if the robot's position real-time update (explained later) is to be used the frequency of the measurements (for the whole scene, not one marker) should be sufficient to avoid delays, for example around 20 Hz.

e) the tool position (held by the robot or surgeon) can be also measured. In this case measuring the robot's position could not be necessary 6. Workstation with navigation software controlling all devices and providing feedback for the surgeon (see FIGS. 2(a)-2(b), 3(a)-3(b)).

a) the navigation software knows about the patient and robot positions. It can measure the tool position (if relevant), b) the navigation software can help the surgeon to find offset between the patient's marker and the vertebrae in the registration process, c) the navigation software can command the robot's position, d) the navigation software controls the robot's position so that the surgeon with the robotic assistance places the screw along the planned trajectory, e) the robot's controller can be external or integrated in the navigation software, f) the navigation software can assist the surgeon in going through phases of the surgery, g) the navigation software can present to the surgeon a graphical feedback: real-time 3D rendering of the measured objects (robot, patient, pointer) and medical images h) the navigation software can integrate interface to the equipment of the operating room like C-Arm, O-Arm. Especially in case of integration with intra-operative medical imaging these devices can provide automatic registration processes and support surgical planning.

i) the navigation software can use different input devices: touchscreen, touchpad, mouse, keyboard, pedals and specialized input devices.

The navigation software may be used to allow the robot to follow any movement of the patient whereby the position is changed. This function may be automatic or on demand.

Example Surgery Workflow (see FIG. 5)

FIG. 1 illustrates the basic elements of the proposed robotic system for spinal surgeries. R corresponds to an active robot, PS corresponds to a passive holding structure, T corresponds to a camera of an optical tracking system, M corresponds to a skull clamp for fixing patient's head. This robotic system corresponds to the one disclosed in applications EP No 11160893.1 filed on Apr. 1, 2011 and PCT application No PCT/IB2012/051607 filed on Apr. 2, 2012 mentioned above and incorporated herein.

Planning for the surgery is based on CT images obtained pre-operatively, as is usual in the present art. Planning can be also done using medical images obtained from different devices (MRI, fluoroscopy, scanners, ultra sound). The CT images must have proper resolution which can be achieved using standard scanners. The surgeon using standard surgical views (Axial, Sagittal, Coronal) and a 3D view defines screw trajectories, natural landmarks (for a point to point registration) and generates 3D model of the vertebrae (for a surface matching and visualization). Data is saved to the file which can be read by the navigation software.

Alternatively, the planning can be done intra-operatively when the user/surgeon defines the trajectories using elements of the system (like pointer or trocar) and saves them for future execution.

Figure 2A:
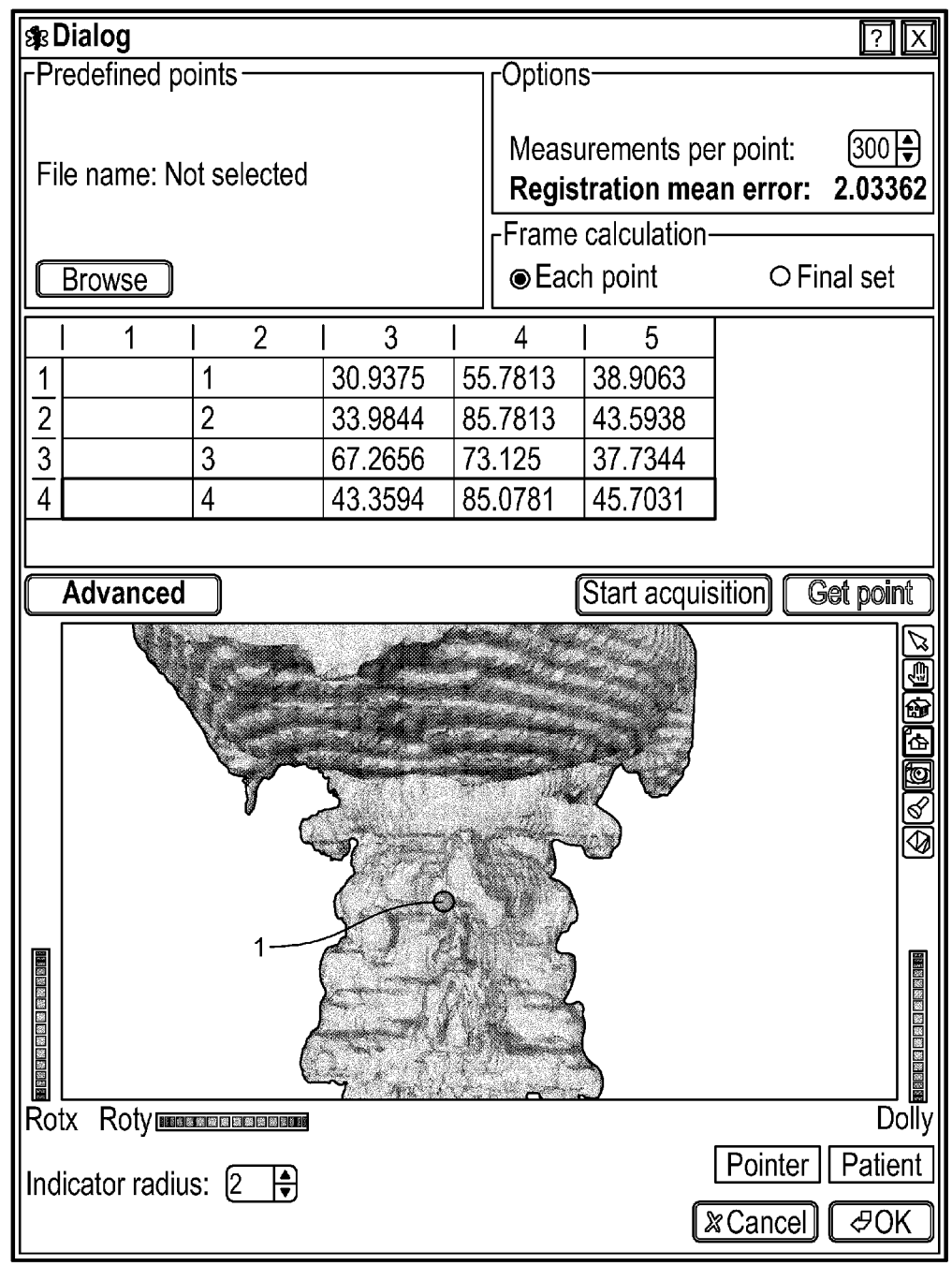
Figure 2B:
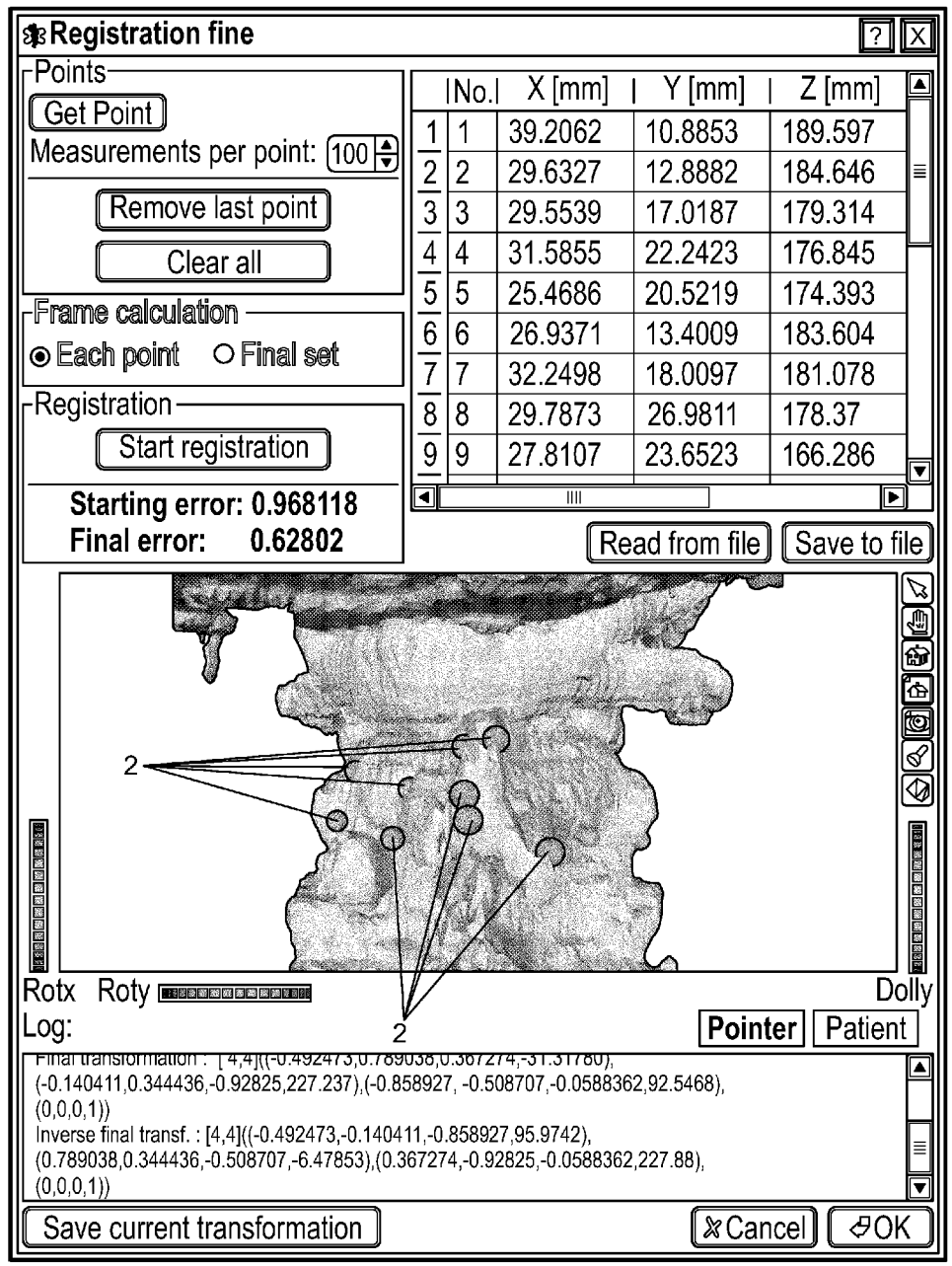

FIG. 2 illustrates the dialogs (screenshots) used during the patient registration typically as presented on the screen of a workstation: specifically, FIG. 2(a) illustrates point to point registration (coarse registration), and FIG. 2(b) illustrates surface matching (fine registration)

During the surgery the patient lies prone with his head fixed in the Mayfield structure M (see FIG. 1). When access to the vertebrae is open, an optical marker of the optical tracking system is attached to it.

Alternatively, patient registration can be done automatically using an intra-operative imaging device.

In the next step the patient's position is registered (the transformation between the vertebrae and attached marker and/or planning is found). Such procedures are known in principle in the art.

Firstly (as a coarse registration) the user/surgeon measures natural landmarks on the vertebrae (using a pointer for example), the same as defined during the planning on images obtained pre-operatively. A navigation software assists him in doing that by showing the natural landmarks on the 3D model (ref FIG. 2a). Specifically, FIG. 2(a) shows a 3D model of the vertebrae (medical images can be used too) with a landmark to be measured shown with a sphere 1. A list of points to be measured is available. User/Surgeon is informed if markers of the optical tracking system are occluded and/or if the precision of the measurement is decreased. A specialized algorithm may be used to find best matching between measured and planned points. The error is shown to the user and if it is sufficiently small the user can proceed to the next step.

The software finds the best correspondence between the set of planned and measured points and shows an estimated error to the surgeon. If the error is acceptable the surgeon can start measuring random points on a surface of the vertebrae (fine registration). When a sufficient number of points is collected (for example 30 points) the navigation software will look for the best match between them and the 3D model of the vertebrae generated during the planning. When the best match is found, the results with an estimated error are shown (ref FIG. 2b). If the error is acceptable the surgery can progress to the next stage, otherwise the registration should be restarted. Specifically, FIG. 2(b) shows the situation where multiple points (illustrated as spheres 2) on the surface of the vertebrae were measured and are added to the 3D model of the vertebrae (medical images can be used too). A list of already measured points is available. The user/surgeon is informed if markers of the optical tracking system are occluded and/or if the precision of the measurement is decreased. Registration is started when a sufficient number of random points is measured and a calculated error is shown to the user.

In the next step the robot R should be positioned using the passive structure PS so that the planned screw trajectory is inside the robot's workspace. The navigation software assists the user/surgeon in doing this task. The user/surgeon unblocks the passive structure and manually moves the robot to the position indicated by the navigation software. The ideal robot position can be shown for example as a semi-transparent phantom (indicator). The phantom is in one color (for example red) at the beginning and changes to another color (for example green) if and when the screw trajectory is inside the robot's workspace. In this case the surgeon can block the passive structure which will rigidly hold the robot in place for the procedure. Of course, other means and procedure can be used to position the robot, for example using haptic principles to indicate to the user when the trajectory is within the working volume. Also other equivalent indicators may be used to position the robot in the proper working volume for the intended procedure.

Figure 3A:
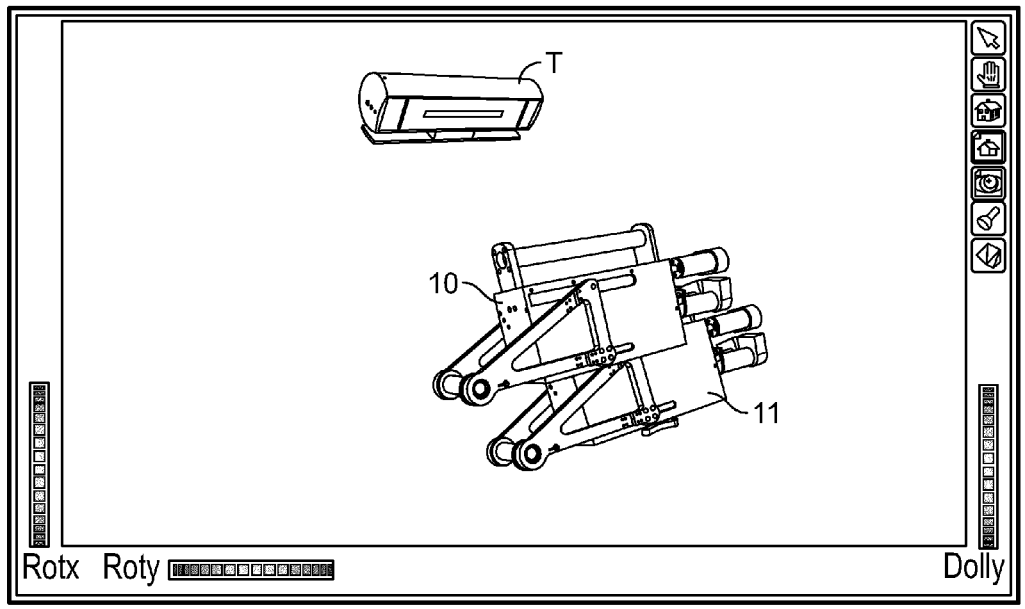
Figure 3B:
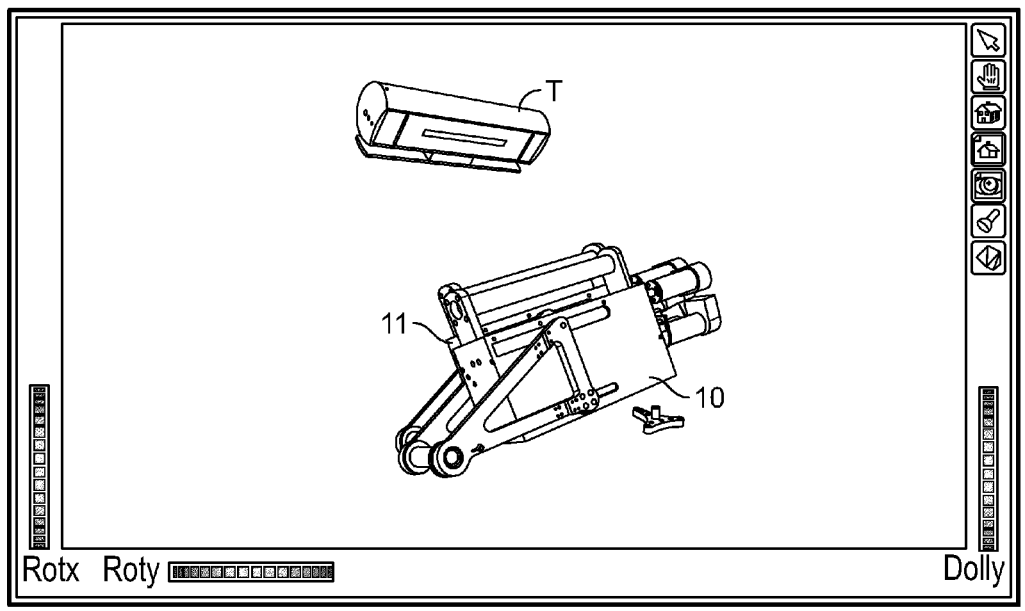

FIG. 3 illustrates exemplary indicators helping the user/surgeon to manually position the robot R after unblocking the passive structure PS. The current robot position 10 is shown for example in grey, the ideal robot position is shown for example as a semi-transparent color indicator, reference 11. If the planned screw trajectory is outside the robot's workspace the indicator is in one color for example red FIG. 3(a), otherwise it takes another color, for example green FIG. 3(b) when the screw trajectory is in the in the working volume.

When the screw trajectory is inside the robot's workspace the robot can start to automatically follow it in real-time i.e. the vertebrae and the robot positions are measured and if of one of them moves the robot will change the position of the tool to compensate. This is an important feature that increases precision, decreases forces exceeded on the vertebrae and is not possible to do manually. This is done by tracking a change of the position of a vertebrae and imposing the same change to the robot. Alternatively, this function may not be automatic but only upon request by the user.

Now the user/surgeon can proceed with the standard surgical procedure which comprises a drilling (using sharpened wire called K-wire), optionally drilling using a canulated drill and a screw placement.

Different procedures can of course be used with other systems (e.g. non-cannulated systems).

FIG. 5 illustrates an example of an embodiment of the method with a block diagram comprising the general steps.

All operations are done through a tube held by the robot (called trocar) which ensures that the screw is placed in the position defined by the robot. After the screw is placed the surgeon can place another screw in the same vertebrae or move to another vertebrae and redo the process.

Different procedures can be applied for percutaneous surgeries.

ENT Surgeries

Background

Some of the ENT (Ear Nose Throat) surgeries comprise the step of removing volumes like tumors, polyps etc. Users/Surgeons use drillers (for bones) and shavers (for soft tissues) which they operate manually. Different tools for tissue removal can be used like lasers, coagulators etc. In many cases they use an endoscopic camera which is not convenient because of a bleeding which drastically decreases the field of view. When the bleeding begins the user/surgeon has to stop the operations, put on a dressing and wait until it stops. For this reason the ENT surgeries take a lot of time. They can be dangerous because when the visibility is constrained important tissues like nerves, orbitals, brain etc. can be destroyed by accident.

System Elements

System elements are similar to the ones used in the spinal surgeries (see above and FIG. 7) with the following changes:

1. Planning:
    b) instead of the screw trajectories the user/surgeon defines volumes that he wants to remove (called "stay-in" zones like tumors, polyps) and volumes that must be protected (called "no-go" zones like nerves, orbitals and other important tissues)
2. Compact robot (see the robotic system disclosed in applications EP No 11160893.1 filed on Apr. 1, 2011 and PCT application No PCT/IB2012/051607 filed on Apr. 2, 2012 mentioned above)
    b) the robot has sufficient number of degrees of freedom to guide the driller or shaver or another surgical tool in space, for example 5 or 6 DOFs.

Additional Points:
    the robot may have force sensor(s) integrated,
    the force sensor(s) may be mounted on the tool tip (for measuring forces on the tool tip) and/or in the tool fixation (for measuring forces on the tool)

1. Robot's controller:
    b) should have control mode suitable for teleoperation
2. Workstation with navigation software ( . . . ):
    d) the navigation software controls the robot's position so that the tool held by the robot (driller or shaver) does not violate the "no-go" zones defined during planning. If the user/surgeon wants to remove certain volumes he should enter it with the tool. Inside such volumes the tool remains blocked inside until he explicitly wants to leave it ("stay-in" zone). There are other way of realizing the concept of "stay-in" and "no-go" zones the idea being to make such procedures safer.

Additional Points:
    the user/surgeon commands the robot positions using a haptic device, the principle of such devices being known in the art
    when the tool approaches the "no-go" zone the user/surgeon feels repulsive/wall-like forces on the haptic device to inform him of the position of the tool
    when the tool is supposed to stay inside the stay-in volume the user/surgeon feels repulsive/wall-like forces that prevent him from leaving the volume as long as it is required
    the margin of interaction around the "no-go" and "stay-in" zones may be defined,
    the coupling between the haptic device movements and the robot movements may be defined to allow the surgeon to have small movements/high precision or big movements/high speed and additional features like tumor removal.

Figure 6:
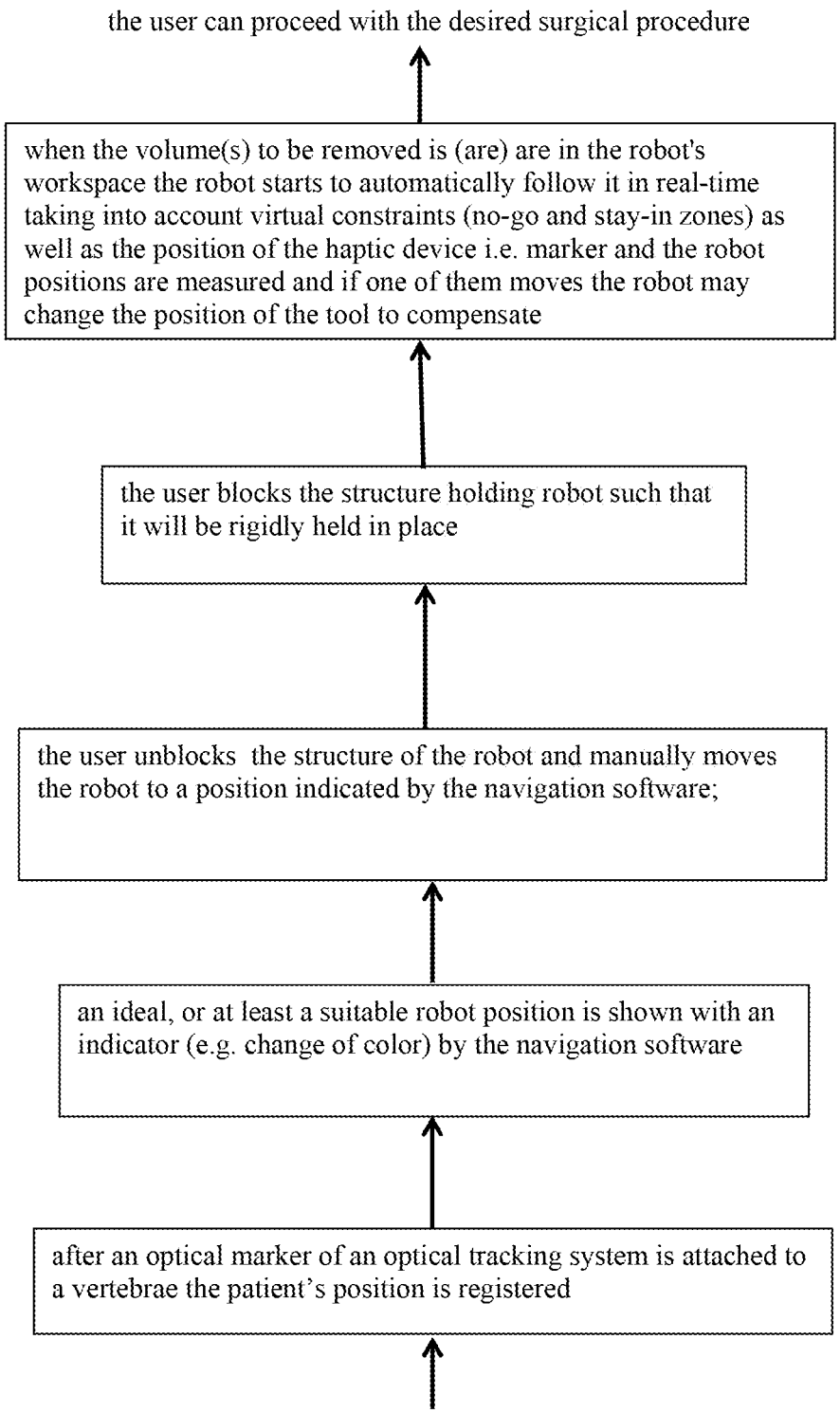
FIG. 6 illustrates a block diagram of the method in another embodiment.

Surgery Workflow (see FIG. 6)

Planning is similar as in the system used for the spinal surgery. Instead of the screw trajectories surgeon should generate models for the "no-go" and "stay-in" zones in the preoperative images. Alternatively, such zones may be defined during the procedure if this is possible or suitable.

Registration and manual robot positioning using passive structure is the same as for the spinal surgery disclosed above.

The tool used in the surgery (for example driller, shaver) should be fixed to the robot R end effector. When desired volumes are inside the robot's workspace the user/surgeon can control the robot position using the haptic device with the assistance of the navigation software.

When approaching a "no-go" zone the user/surgeon a feels repulsive force on the haptic device which prevents him from touching important tissues.

When he enters a "stay-in" zone he remains blocked inside said zone until he explicitly wants to leave. He can move the tool inside the volume and follow for example virtual tumor walls felt on the haptic device until he is sure to remove all needed tissue. The margins of interaction with walls can be defined so for example it is possible to remove 80% of the tumor or 120% (tumor and tissues around). The coupling between the haptic device and the robot movements can be defined so that the surgeon can have small movements/high precision or big movements/high speed. Other algorithms for controlling the haptic device can be implemented.

High bleeding can be accepted as it does not disturb the robot operation (the robot and patient positions are measured by the optical tracking so there is no need for endoscope except from control and verification). As tumor can be removed fast (in few minutes) high bleeding during a short time for patient can be accepted.

Figure 4:
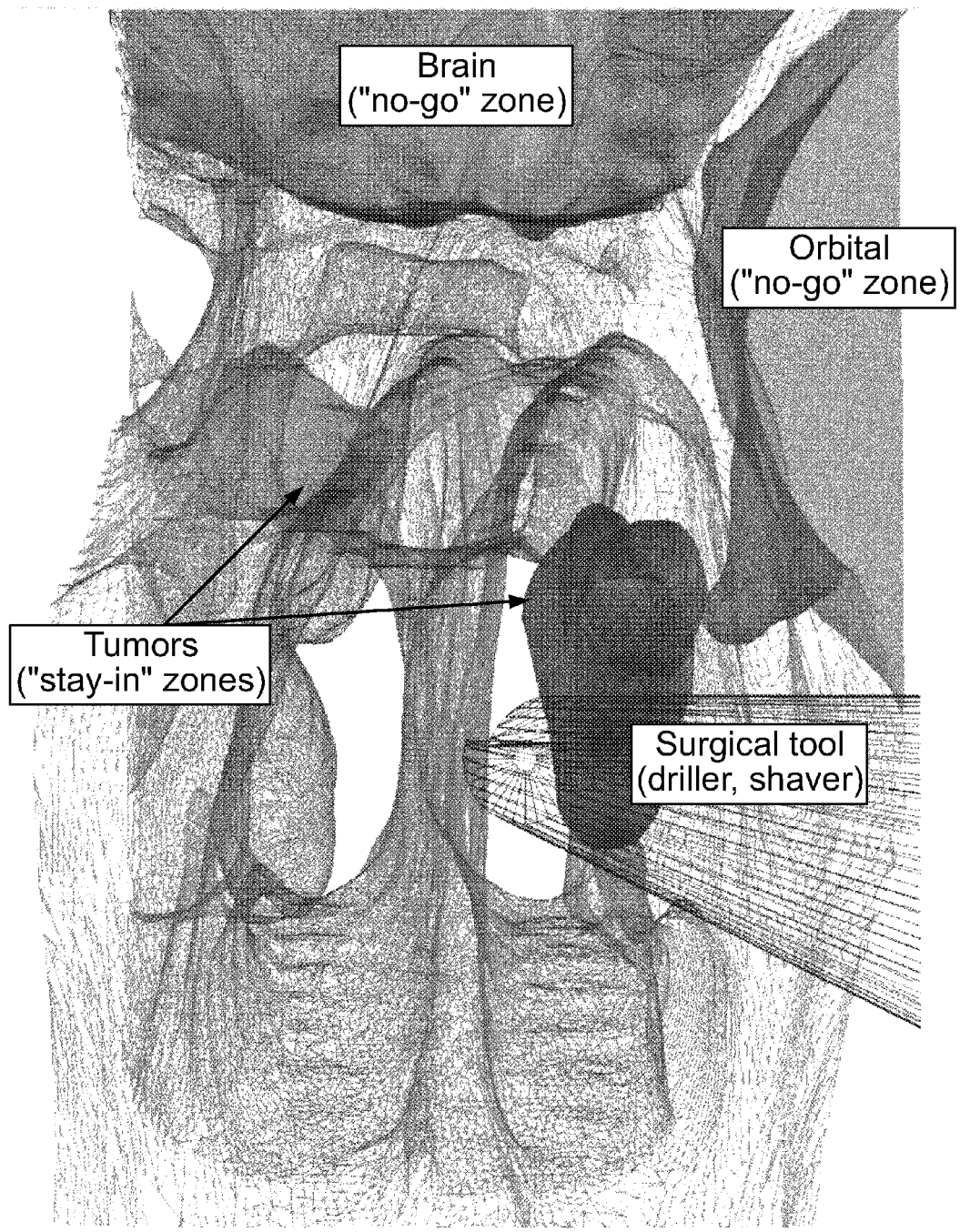
FIG. 4 illustrate a screenshot of an ENT surgical procedure.

FIG. 4 illustrates screenshots of the navigation software used in the ENT surgery. The surgeon controls the tool position using a haptic device. He can feel repulsive forces when he approaches the "no-go zones" and he can stay inside the "stay-in zone" until he is sure to remove all needed tissue.

FIG. 6 illustrates an example of an embodiment of the method with a block diagram comprising the general steps.

Figure 7:
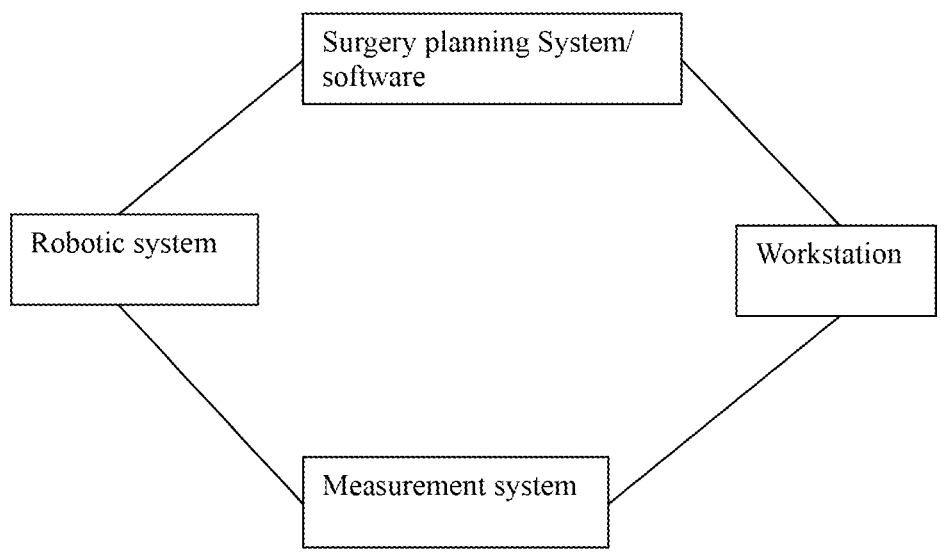
FIG. 7 illustrates a block diagram of the system according to the invention.

FIG. 7 illustrates in block-diagram an example of a system of the invention with the different elements forming a system suitable for carrying out the method. As defined hereabove, the system comprises at least a surgery and planning system, a robotic system, a measurement system and a workstation, such as a computer station.

The examples and values (sizes, DOF etc) given in the above description are only for illustrative purposes and should not be construed in a limiting manner on the scope of the invention. Also, equivalent means may be envisaged by a skilled person and the embodiments described herein may also be combined as desired.

What is claimed:

1. A robotic surgical system for assisting a surgeon in preparing a hole in a spine of a patient and placing a screw in the hole during an operation, the system comprising:
    a robot comprising an end-effector for holding a surgical tool for use in drilling the hole and placing the screw in a vertebra of the patient;
    a controller for controlling the position of the end-effector, wherein the end-effector can be manually and freely positioned by the surgeon during the operation; and
    a measurement system with a computer processor for:
        measuring, by the processor, a position of the vertebra of the patient;

determining, by the processor, a change in the position of the vertebra; and automatically adjusting, via the robot, the position of the end-effector based at least in part on a change in the position of the vertebra determined by the processor such that a spatial relationship between the end-effector and the vertebra remains substantially unaltered as at least a portion of the operation is performed, thereby ensuring the surgical tool remains aligned with a trajectory as a hole in the vertebra is prepared and a screw is placed in the hole.

2. The system of claim 1, wherein the robot allows positioning of the surgical tool by the surgeon with at least four degrees of freedom.

3. The system of claim 1, wherein the position of the vertebra is a position of a marker placed in spatial relation to the vertebra.

4. The system of claim 1, wherein the measurement system is an optical tracking system comprising a camera; an electro-magnetic tracking system; fixed measurement system; or template-based tracking system.

5. The system of claim 4, wherein the measurement system comprises a first marker attached to the robotic surgical system and a second marker configured to attach to the patient.

6. The system of claim 5, wherein the measurement system is the optical tracking system and the optical tracking system comprises a pointer that can be used to measure a single point in space.

7. The system of claim 1, comprising a force sensor for measuring forces on the surgical tool.

8. The system of claim 7, wherein the force sensor is mounted on the end-effector.

9. The system of claim 1, wherein the robotic surgical system comprises a display for providing graphical feedback to the surgeon.

10. The system of claim 1, wherein the surgical tool is a tube.

11. The system of claim 1, wherein the robotic surgical system comprises a passive structure that rigidly holds the robot in place.

12. The system of claim 1, wherein the measurement system is configured to provide real-time patient and robot position measurements and position tracking.

13. The system of claim 1, wherein the controller is arranged such that the surgeon can manually and freely position the robot in space using hands-on control.

14. The system of claim 1, wherein the controller permits gross manual positioning of the end-effector.

15. The system of claim 1, wherein the robot comprises a passive structure.

16. The system of claim 15, wherein the passive structure can be manually and freely positioned by the surgeon during the operation.

17. The system of claim 16, wherein the passive structure can be blocked by the surgeon such that the robot is rigidly held in place.

* * * * *